US00PP36830P2

(12) United States Plant Patent
Kramer

(10) Patent No.: US PP36,830 P2
(45) Date of Patent: Jul. 15, 2025

(54) ***HOSTA* PLANT NAMED 'NK2021'**

(50) Latin Name: ***Hosta* hybrid**
Varietal Denomination: NK2021

(71) Applicant: Ninja Kramer, Væggerløse (DK)

(72) Inventor: Ninja Kramer, Væggerløse (DK)

( * ) Notice: Subject to any disclaimer, the term of this patent is extended or adjusted under 35 U.S.C. 154(b) by 0 days.

(21) Appl. No.: 18/966,052

(22) Filed: Dec. 2, 2024

Related U.S. Application Data

(60) Provisional application No. 63/646,486, filed on May 13, 2024.

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
CPC ... A01H 5/12; A01H 5/02; A01H 5/00; A01H 6/12
See application file for complete search history.

*Primary Examiner* — June Hwu
(74) *Attorney, Agent, or Firm* — Penny J. Aguirre

(57) ABSTRACT

A new cultivar of *Hosta* plant named 'NK2021' that is characterized by its unique foliage colors with green margins with red centers throughout the growing season with spring foliage green and flushed with red marking and late spring into autumn foliage having deep red centers with dark green margins, its flowers that are purple color, its flowers that bloom from late summer to early autumn, its low growing and low maintenance plant habit, and its petioles that are red in color.

2 Drawing Sheets

Botanical classification: *Hosta* hybrid.
Cultivar designation: 'NK2021'.

BACKGROUND OF THE INVENTION

The present invention relates to a new and distinct cultivar of *Hosta* plant of hybrid origin and will be referred to hereafter by its cultivar name, 'NK2021'. 'NK2021' represents a new *Hosta* grown for use as a landscape plant.

The Inventor discovered the new cultivar in summer of 2000 as a naturally occurring chimeral mutation of *Hosta* 'First Blush' (U.S. Plant Pat. No. 28,920) that was growing in a container outdoors in a containerized production block of 'First Blush' in Falster, Denmark.

Asexual propagation of the new cultivar was first accomplished by division by the Inventor in Falster, Denmark in spring of 2021. Asexual propagation of the new cultivar by division and tissue culture using meristematic tissue has shown that the unique features are stable and reproduced true to type in successive generations.

SUMMARY OF THE INVENTION

The following traits have been repeatedly observed and represent the characteristics of the new cultivar. These attributes in combination distinguish 'NK2021' as a new and unique cultivar of *Hosta*.

1. 'NK2021' exhibits unique foliage colors with green margins with red centers throughout the growing season with spring foliage green and flushed with red marking and late spring into autumn foliage having deep red centers with dark green margins.
2. 'NK2021' exhibits flowers that are purple color.
3. 'NK2021' exhibits flowers that bloom from late summer to early autumn.

4. 'NK2021' exhibits a low growing, low maintenance plant habit.
5. 'NK2021' exhibits petioles that are red in color.

The parent plant of 'NK2021' is similar to 'NK2021' in plant habit, plant size, flower color, and petiole color. The parent plant differs from 'NK2021' in having leaves that are wider and have less red color that is lighter on the leaves with the red coloration only present in the spring. 'NK2021' can be most closely compared to *Hosta* hybrid cultivars 'Bloodline' (not patented) and 'Holar Purple Flash' (not patented). 'Bloodline' differs from 'NK2021' in having a taller plant height and foliage that it green and flushed with faded red-purple in a different pattern. 'Holar Purple Flash' differs from 'NK2021' in having green leaves with a purple hue towards the red petioles, a slightly taller plant height, and leaves that are more broad.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include a website listings by Mr. Plant Geek (facebook).

BRIEF DESCRIPTION OF THE DRAWINGS

The accompanying color photographs illustrate the overall appearance and distinct characteristics of the new *Hosta*.

The photographs were of plants grown in an unheated greenhouse in 17-cm containers in Heerhugowaard, The Netherlands.

Figure 1:
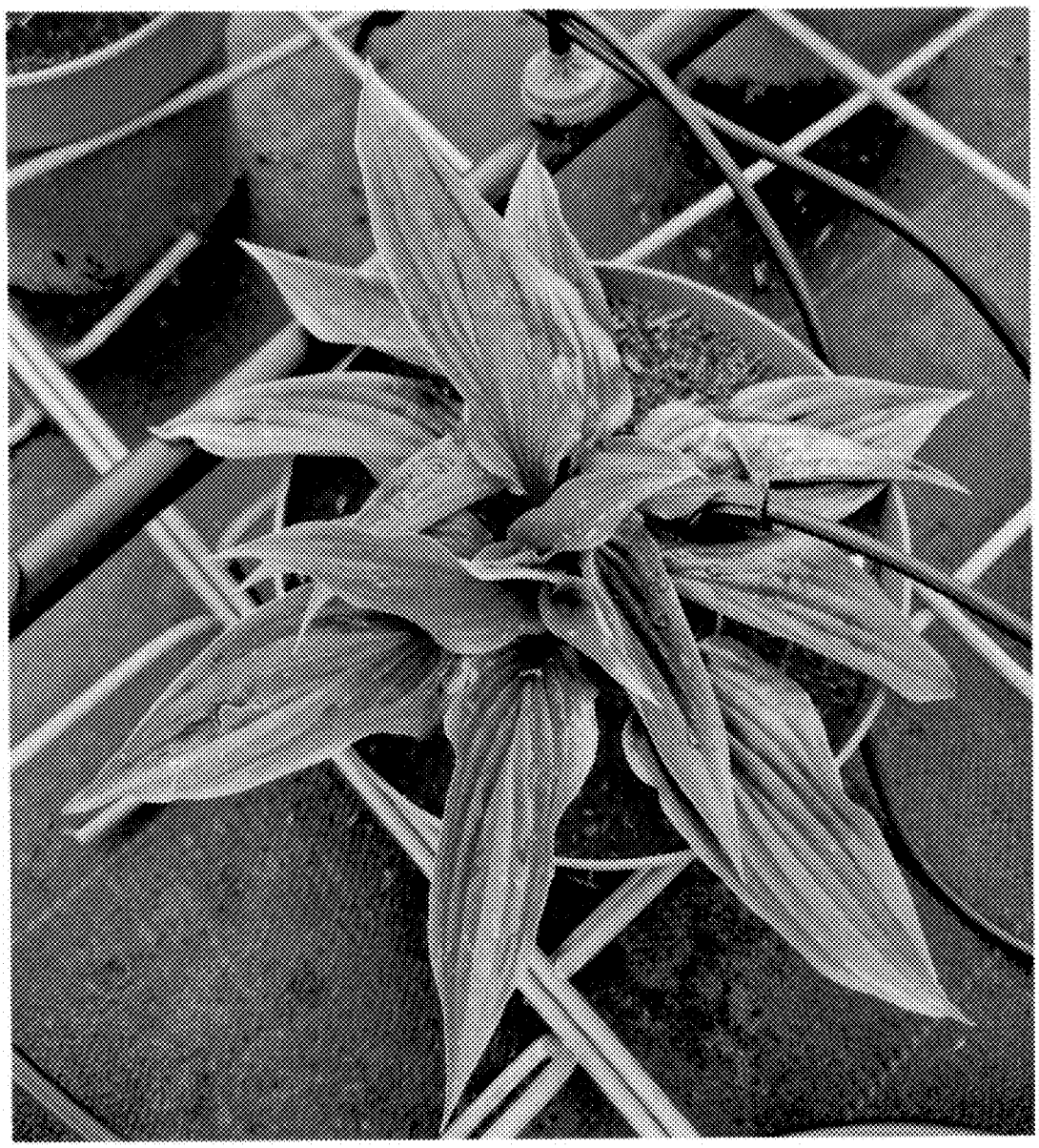
FIG. 1 provides a view of the spring foliage a 22-week-old plant of 'NK2021'.
Figure 2:
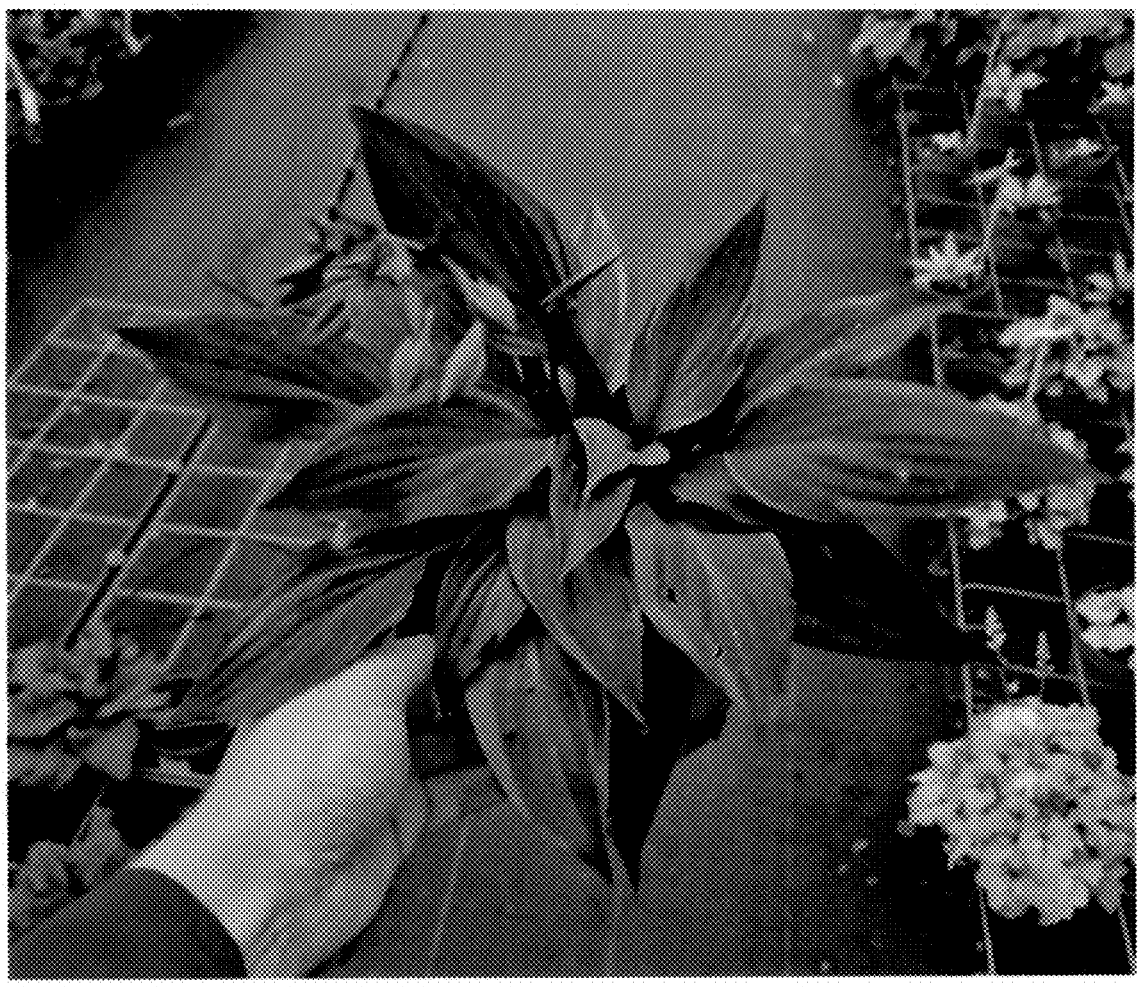

The photograph in FIG. 2 provides a view of the autumn foliage of a 50-week-old plant of 'NK2021' in bloom.

The colors in the photographs may differ slightly from the color values cited in the detailed botanical description, which accurately describe the colors of the new *Hosta.*

DETAILED BOTANICAL DESCRIPTION OF THE PLANT

The following is a detailed description of 1.5 year-old plants as grown outdoors in 19-cm containers in Heerhugowaard, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—August to October in The Netherlands.

*Plant type.*—Herbaceous perennial.

*Plant habit.*—Short, broadly spreading with mostly upright blooming stems.

*Height and spread.*—Reaches 30 to 35 cm in height in height and spread when grown in the landscape.

*Cold hardiness.*—At least in U.S.D.A. Zones 5.

*Diseases and pests.*—No susceptibility or resistance to diseases or pests has been observed.

*Root description.*—Freely branched, fleshy.

*Propagation.*—Tissue culture and division.

*Root development.*—In tissue culture; 10 weeks to produce a rooted plug and 10 weeks to produce a fully rooted plant in a P9 container from a tissue culture plug.

*Growth rate.*—Moderately vigorous.

Foliage description:

*Leaf shape.*—Ovate.

*Leaf division.*—Simple.

*Leaf base.*—Rounded.

*Leaf apex.*—Acute.

*Leaf venation.*—Camptodrome pattern, 6 pairs of veins, upper surface color; veins match the leaf surface color with base 187B, lower surface color; most of the veins match the leaf surface color, tip 187B and base 187D.

*Leaf margins.*—Entire, degree of undulation; weak to medium.

*Leaf attachment.*—Petiolate.

*Leaf arrangement.*—Alternate, in basal rosettes.

*Leaf surface.*—Upper and lower surface is glabrous, smooth, very slightly glossy and leathery, non-rugose, matte.

*Degree of leaf bulging between veins.*—Medium.

*Degree of leaf twisting.*—Absent to weak.

*Degree of leaf blistering.*—Absent.

*Position of broadest part of leaf.*—Slightly towards the base.

*Leaf orientation.*—Held nearly upright to slightly outward on upright petioles.

*Leaf color.*—Emerging (scaly) before opening; 144A, young upper surface; 144A, base 187B, tip 187A, young lower surface; 138B, base 179B to 179C, tip 187A, mature upper surface; 144A, center 187A to 187B, flushed with 187A, sides N187A, mature lower surface; 137B, base 187B to 187C.

*Leaf size.*—Average of 14 cm in length and 6.7 cm in width.

*Leaf quantity.*—Average of 50 per plant.

*Petioles.*—Strong, average of 8 cm in length, average of 1.3 cm in diameter, both surfaces are very slightly glossy, color; upper surface 187B, lower surface 187C to 187D, shape of inner side in cross section; moderately V-shaped.

Flower description:

*Inflorescence type.*—Terminal racemes of single open trumpet-shaped flowers.

*Inflorescence size.*—23 cm in height, 15 cm in width.

*Lastingness of inflorescence.*—About 4 weeks from first opening bloom to fading of last opening bloom, individual blooms last up to 5 days, self cleaning.

*Flower type.*—Trumpet, single.

*Flower/inflorescence number.*—Average of 2 inflorescences per plant, 12 flowers per inflorescence.

*Flower fragrance.*—None.

*Flower aspect.*—Held horizontal to slightly drooping.

*Flower buds.*—Average of 1.5 cm in length, 6 mm in diameter, oblong in shape, smooth, glabrous and moderately glossy surface, color; 79A to 79B, flushed with 145B.

*Flower size.*—Average of 5 cm in depth and 4.5 cm in diameter.

*Peduncles.*—An average of 20 cm in length, 3 mm in diamter, held in an average angle of 10°, strong, smooth and glabrous surface, 187A in color.

*Pedicels.*—An average of 1.7 cm in length, 2 mm in diamter, held in an average angle of 70°, moderately strong, smooth and glabrous surface, color; 187B to 187C.

*Tepals.*—6, rotate, fused into campanulate shape, 60% of the tepals are fused at base into tube, glabrous, slightly glossy and dull surfaces, entire margins, acute apex, 5 cm in length (including tube 3.3 cm in length), 9 mm in width, color; when opening upper and lower surface N82B to N82D, fully open upper surface N82D, inner surface of tube N82C, veins N82A, fully open lower surface 85A to 85B, outer surface of tube 81B, veins 86D.

*Floral bracts.*—At the base of each pedicel, ovate in shape, acute apex, truncate base, both surfaces are smooth and glabrous, average of 2 cm in length and 5 mm in width, color; 79A and 144A.

Reproductive organs:

*Gynoecium.*—Pistil; 1, 4 cm in length, style and stigma; not distinguishable, ovary; 6 mm in length, 2 mm in width, 145B in color.

*Androecium.*—Stamens; 6, filament; 5 cm in length, 1 mm in diameter, NN155B in color, 157D at the base, anthers; elliptic in shape, 2 mm in length, 1 mm in width, N187A to 187B in color, pollen is low in quantity and 14B in color.

*Fruit/seed.*—Production of seed capsules has not been observed to date.

It is claimed:

1. A new and distinct cultivar of *Hosta* plant named 'NK2021' as herein illustrated and described.

* * * * *